United States Patent [19]

Panster et al.

[11] Patent Number: 4,647,679

[45] Date of Patent: Mar. 3, 1987

[54] PLATINUM AND/OR PALLADIUM CONTAINING ORGANOPOLYSILOXANE-AMMONIUM COMPOUNDS, METHOD FOR THEIR PREPARATION AND USES

[75] Inventors: Peter Panster; Marlies Englisch, both of Rodenbach; Peter Kleinschmit, Hanau, all of Fed. Rep. of Germany

[73] Assignee: Degussa Aktiengesellschaft, Frankfurt, Fed. Rep. of Germany

[21] Appl. No.: 699,968

[22] Filed: Feb. 8, 1985

[30] Foreign Application Priority Data

Feb. 10, 1984 [DE] Fed. Rep. of Germany ....... 3404702

[51] Int. Cl.$^4$ .............................................. C07F 15/00
[52] U.S. Cl. ........................................... 556/9; 556/10
[58] Field of Search ..................................., 556/9, 10

[56] References Cited

U.S. PATENT DOCUMENTS

| | | | |
|---|---|---|---|
| 2,823,218 | 2/1958 | Speier et al. | 556/9 X |
| 3,419,593 | 12/1968 | Willing | 556/9 X |
| 3,637,775 | 1/1972 | Yates | 556/10 |
| 3,775,452 | 11/1973 | Karstedt | 556/10 |
| 3,795,656 | 3/1974 | Martin | 556/9 X |
| 4,365,030 | 12/1982 | Oswald et al. | 556/9 X |
| 4,398,010 | 8/1983 | Adkins | 556/9 X |

*Primary Examiner*—Helen M. S. Sneed
*Attorney, Agent, or Firm*—Beveridge, DeGrandi & Weilacher

[57] ABSTRACT

Platinum and/or palladium containing organopolysiloxane-ammonium compounds containing units represented by the structural formula:

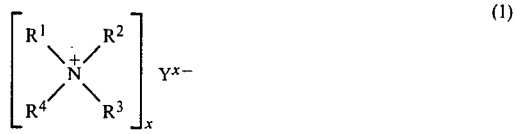

(1)

in which $R^1$, $R^2$ and $R^3$ represent:

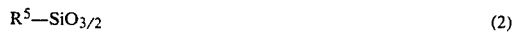

(2)

wherein $R^5$ is an alkylene group and the free valences of oxygen are satisfied by silicon atom and additional groups of the structural formula (2), optionally with the introduction of a crosslinking agent,
$R^4$ can be $R^1$, $R^2$, $R^3$ or hydrogen, alkyl, cycloalkyl or benzyl,
$Y^{x-}$ is $MeX_4^{2-}$ or $MeX_6^{2-}$, wherein Me is platinum or palladium and
X is chlorine or bromine, and can further denote a 1 to 3 valent anion of a protonic acid capable of forming a stable salt with an amine, or the hydroxy group, and
x is a number from 1 to 3. Methods for the obtaining the polymeric organosiloxane-ammonium-noble metal complexes and as well as the use thereof as catalysts for hydrosilylation and hydrogenation reactions are disclosed.

23 Claims, No Drawings

PLATINUM AND/OR PALLADIUM CONTAINING ORGANOPOLYSILOXANE-AMMONIUM COMPOUNDS, METHOD FOR THEIR PREPARATION AND USES

The present invention relates to new platinum and/or palladium containing organopolysiloxane-ammonium compounds in which the platinum and/or the palladium are bound in complex anionic form onto an organopolysiloxane matrix. The noble metal containing systems which are insoluble in water and organic solvents are valuable catalyst systems for hydrosilylation and hydrogenation reactions which partly because of a high activity as well as selectively are outstanding and can be synthesized in a simple manner as well as after treated in an expeditious manner. Methods for the preparation and after treatment of these new compounds are described herein.

Noble metal compounds which are bound through covalent or ionic bonds onto an insoluble polymer matrix demonstrate, from a theoretical viewpoint, when introduced as catalyst systems, a series of advantages as compared to comparable soluble compounds that are introduced as catalysts: In addition to the fundamentally easier separation of the noble metal containing compounds from the product or substrate and the recycling thereof, the valuable noble metal is more easily recuperated, the catalytic life time can be lengthened and the corrosive action of the frequently saline metal compounds can be substantially reduced. Intensive work has been done and is being carried out in this field by many workers and the level of the technology of this art may be seen in several survey articles, for example, D. D. Whitehurst in CHEMTECH, January 1980, p. 44; R. H. Grubbs, CHEMTECH, August 1977, p. 512; D. C. Bailey and S. H. Langer in Chem. Rev., Vol. 81, 2, 109 (1981).

For the matrix as well as the carrier material, there have been used for this purpose primarily organic polymer systems such as polystyrol. These have shown in general, however, a lack of the qualities which should be observed in a good catalyst carrier because they do not possess a solid fixed structure, the conformation thereof and with that the surface area as well as volume of the individual particles is strongly dependent on external parameters such as temperature, pressure and solvent material. The swelling of the carrier in the selected solvents is particularly important in order to obtain a penetration of the reactants to the catalyst center and to make certain that the reaction velocity is not permitted to be controlled by diffusion. The high mobility of the matrix also permits the coming together of the fixed metal moieties so that an undesired creation of a catalytically inactive multiple particle complex is possible. The result therefore is that there can also occur a dissolution of the polymer matrix itself in the employed reaction medium in an unwanted and undesired manner.

Inorganic polymer systems such as, for example, silicas, silica gels or aluminum oxide, are similar in principle by reason of their fixed rigid structure, their fundamentally higher temperature resistance and aging resistance, their easy accessibility of the fixed metal moities, and are therefore fundamentally better for these reasons, nevertheless without exception they possess a very grave disadvantage insofar as the quantity of functional groups by which a fixation of metal bonds can take place is relatively low, so that much carrier ballast must be carried around with the catalyst.

In the recent past, there have been developed catalyst systems such as described in German OLS Nos. 30 29 599 and 31 31 954 of metal combinations with covalent donor acceptor bonds which can be fixed on carriers which are made from insoluble organopolysiloxanes, for example, phosphor or nitrogen containing organopolysiloxanes and in accordance with expectations, these also possess the good properties of inorganic carriers but not their disadvantages. As a result of that, they permit themselves to be prepared in a substantially custom fit manner, for example, through introduction of a crosslinking agents or co-catalysts.

It is of particular interest, and therefore the object of the present invention, to provide for the development of a system on the basis of platinum and/or palladium by which complex anionic compounds of these two metals are bound to an ammonium group containing organopolysiloxane carrier by ionic bonds. Platinum containing organopolysiloxanes are described in the German Pat. No. 24 00 039, however, they are soluble compounds and which because of that also contain the above referred to disadvantages which arise with use as a catalyst.

The platinum and palladium containing polymeric organosiloxane-ammonium compounds of the present invention are therefore characterized in that they contain moities of the general formula:

in which $R^1$, $R^2$ and $R^3$ each represents a group of the general formula:

in which $R^5$ represents an alkylene group from 1 to 12 carbon atoms, a cycloalkylene group with 5, 7 or 8 carbon atoms or a moiety represented by the structural formula:

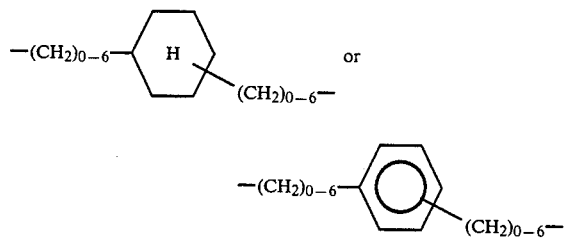

and wherein $R^1$, $R^2$ and $R^3$ can be the same or different, and the free valences of the oxygen atoms are saturated by either silicon atoms or additional groups of the formula (2) and/or crosslinking bridging agents of the formula:

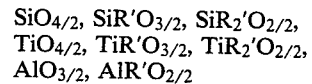

wherein R' is methyl or ethyl, the ratio between the silicon atoms in formula (2) and the bridging atoms silicon, titanium and aluminum ranges from 1:0 to 1:10, $R^4$ has the same meaning as $R^1$, $R^2$ and $R^3$ or can be hydrogen, a 1 to 10 carbon atom containing linear or branched chain alkyl group, a 5 to 8 carbon atom containing cycloalkyl or a benzyl group and $Y^{x-}$ represents:
$PtCl_4^{2-}$, $PtCl_6^{2-}$,
$PtBr_4^{2-}$, $PtBr_6^{2-}$,
$PdCl_4^{2-}$, $PdCl_6^{2-}$,
$PdBr_4^{2-}$, $PdBr_6^{2-}$ and for an inorganic or organic 1 to 3 valent anion of an inorganic or organic protonic acid which is capable of forming a stable salt with an amine base, or a hydroxy group and x is a number from 1 to 3.

It has been demonstrated that $R^5$ can be a linear or branched chain alkylene group without there appearing considerable material difference in the end product.

In the polymer chain, there can be a multiplicity of complex anions of platinum and/or palladium arranged next to each other, the molecular ratio between the platinum and/or palladium contents to the rest of the inorganic and organic anions should advantageously lie in the range of 1:0 to 1:100.

Typical examples of inorganic or organic anions, which can be in addition to the complex anions of platinum and/or palladium in the polymer combination are halogenides, hydroxides, hypochlorite, sulfate, hydrogen sulfate, nitrite, nitrate, phosphate, carbonate, hydrogen carbonate, chlorate, perchlorate, chromate, dichromate, cyanide, rhodanide, sulfide, hydrogen sulfide, selenide, telluride, borate, metaborate, azide, tetrafluoroborate, tetraphenylborate, hexafluorophosphate, acetate, propionate, oxalate, trifluoroacetate, trichloroacetate or benzoate. In particular, it is advantageous to use the chloride, bromide, iodide, hydroxide, sulfate, hydrogen sulfate, nitrate, carbonate, hydrogen carbonate and tetrafluoroborate.

The introduction of the silicon-, titanium-, or aluminum-containing crosslinking agent serves to control the platinum and/or palladium density in the solid material, to control the porosity which in turn has a definite influence on the selectivity of the catalyst, and a control over the surface area properties and in particular, the hydrophilicity and hydrophobicity. In addition to that, the crosslinking agent can also take over the function of a so-called activator or cocatalyst.

Particularly preferred from the standpoint of thermal stability and inertness relative to chemical attacking agents, in particular with respect to bases, are the polymeric ammonium compounds according to formula (1) wherein $R^1$, $R^2$ and $R^3$ have the same meaning and especially when $R^1$, $R^2$ and $R^3$ are identical. According to an advantageous embodiment of the invention, $R^1$, $R^2$ and $R^3$ are each identical and $R^4$ is methyl.

Particular advantages with respect to the utility of the starting materials and the material properties of the polymeric platinum and palladium containing organosiloxane-ammonium compounds reside in the compounds which are created from polymeric moities of the formula:

[(H_3C)N(CH_2CH_2CH_2SiO_{3/2})_3]_x^+ Y^{x-} in which $Y^{x-}$ has the same scope of meaning as set forth in formula (1) above.

In view of the introduction of the platinum and/or palladium containing organopolysiloxane-ammonium compounds as catalyst systems, it has been demonstrated often as particularly advantageous especially with respect to the activity and also with regard to the selectivity that these compounds be chemically modified after their synthesis. This modification resides in the lowering of the oxidation level of the bound platinum and/or palladium.

According to this, there is utilized a conversion with a reducing agent such as formaldehyde, hydrazine, alkali- or alkaline earth metal borhydride, boran compounds, aluminum hydrides, aluminum alkyls, hydrogen and hydrogen silanes or alcohols at a total pressure of 1 to 300 bar in a temperature range of $-100°$ to $350°$ C.

It is a further object of the invention to provide methods for the preparation of platinum and/or palladium containing organopolysiloxane-ammonium compounds. One method is carried out utilizing an organopolysiloxane-ammonium compound as described in DE-OS No. 31 20 195 consisting of an entity of formula (1) wherein $Y^{x-}$ is chosen to be a 1 to 3 valent anion of an inorganic or organic protonic acid which is treated with a stoichiometrically excess amount or an amount less than the stoichiometric of the compound:

$M_2PtCl_4$, $M_2PtCl_6$
$M_2PtBr_4$, $M_2PtBr_6$
$M_2PdCl_4$, $M_2PdCl_6$
$M_2PdBr_4$, $M_2PdBr_6$ optionally containing water of crystallization, the crystalline hydrated form thereof wherein M represents lithium, sodium, potassium, ammonium or hydrogen, in water or a polar organic solvent material wherein the platinum and/or palladium compounds are at least partially soluble therein, in order to mutually exchange, either partially or completely, the anions according to known static or dynamic principles, the metal containing solid material obtained thereby subsequently being washed, optionally separating the solid from the liquid phase and optionally drying, as well as in any desired sequence, grinding, classifying and tempering. The drying of the exchanged product can take place at a temperature of room temperature up to 250° C., optionally even under the influence of vacuum. The grinding of the solid material can, of course, be carried out before the obtaining of the complex platinum or palladium anion in dry form or in a suspension form. Hereby, it is understandable that the exchange can be accelerated, however because of the fineness of the solid material particle size this can only be carried out according to the known dynamic principles which are applicable. Of course, the grinding can also be carried out during, or shortly after, the ion exchange.

A tempering of the product can be shown to result in an increase in the stability of the matrix and is therefore often desirable. This consists of a temperature treatment by heating at 150° to 400° C. over a duration of at least 1 hour up to 4 days and, optionally, with the use of vaccum.

Although water is the preferred reaction medium in which the introduction of the complex platinum and/or palladium anion can be carried out, there are for this purpose in principle also other solvent materials capable of being used which, because of the solubility of the metal starting compounds that are utilized and those alkali metal salts which are obtained as side products, must be of a very polar nature. The suitable solvent materials are, for example, methanol, ethanol, n- and i-propanol, acetone, dimethylformamide, dimethylsulfoxide, hexamethylphosphoric acid triamide, aliphatic or aromatic nitro compounds or nitrile or mixtures thereof with water.

The temperature at which the introduction of the complex platinum or palladium anions can be carried out is not to be considered as particularly critical, because it can in principle be above or below room temperature. In regard to a particularly rapid exchange of ions, it is of course advantageous to work above room temperature in a temperature range of 30° to 250° C. in which there may be optionally utilized super pressure which is the sum of the partial pressures of the components of the reaction mixture at the utilized temperature.

The choice of the stoichiometric relationship between the introduced organopolysiloxane-ammonium compounds and the platinum and/or palladium compounds depends upon, as may be readily comprehended, whether a saturation or only a partial saturation of the polymeric solid material with complex platinum and/or palladium anions is to be accomplished, which in turn has an influence on the catalytic properties of the catalyst which is then obtained. Should a saturation be desired to be obtained, then there will suffice in principle an exchange equilibrium stoichiometric amounts of both components for the conversion.

With regard to a rapid carrying out of the exchange, a slight excess of the noble metal containing reactant is advantageous. In the case of a desired partial exchange, a calculation of the stoichiometric amounts of the organopolysiloxane-ammonium compound and the platinum and/or palladium containing starting material based on the partial exchange is carried out.

For the preparation of the organopolysiloxane-ammonium compounds, which contain multiple complex anions of platinum and/or palladium, the conversion of the platinum and/or palladium starting materials with the organopolysiloxane-ammonium compound of formula (1) wherein $Y^{x-}$ is a 1 to 3 valent anion of an inorganic or organic protonic acid can be carried out simultaneously or in a stepwise manner, wherein the ultimately obtained metal containing solid material can be separated from the liquid phase, washed, and dried, optionally after each conversion and in any desired reaction sequence and, if desired, optionally tempered.

In both variation, there is to be achieved the previously described stoichiometry through the desired exchange gradient and the desired platinum/palladium relationship. In the case of the simultaneous conversion, the previously described measures are carried out after the exchange reaction. In the stepwise conversion, the after treatment steps can be carried out after the first exchange reaction, however, it is reasonable that the partially exchanged organosiloxane-ammonium compound be washed only and immediately thereafter conducted through the second exchange step. The combination of both metal platinum and palladium in a organopolysiloxane-ammonium compound can advantageously effect the activity or the selectivity.

In carrying out the ion exchange according to the aforementioned dynamic principle, the conversion of the initial polymeric ammonium compound with at least partially dissolved platinum and/or palladium compound is conducted in an aqueous suspension or in an organic suspension medium with vigorous agitation of both components. Subsequently, the solid material is separated off and, optionally, is again stirred with a fresh solution of its co-reactant. This procedure is repeated so often until the ion exchange to the desired degree is fully carried out. Subsequently, the solid material can be treated according to existing processing techniques such as filtration, centrifugation and/or decantation to achieve separation, and is thereafter washed until salt-free, and is then dried at room temperature or at elevated temperature up to 250° C., optionally under vaccum, and tempered at a temperature of 150° to 400° C. temperature, and then ground as well as classified.

In carrying out the invention according to static principles, the initial polymeric ammonium compound is used as an exchange bed and is brought into contact with a solution containing at least partially dissolved platinum and/or palladium containing reaction components.

If one operates using an ion exchange column as the ion exchange bed, then in order to obtain the desired through flow, it is necessary that the polymeric initial product be of a determined minimum particle size. Overall, this is carried out with a laboratory column and using a minimum particle size of 0.2 mm. After a complete exchange, there is also a washing carried out until a salt-free product is obtained and it can then either be treated according to after treatment measures or further processing steps can be carried out.

The after treatment of the formed platinum and/or palladium containing organopolysiloxane-ammonium compounds with reducing agents can be directly carried out after the said preparation in suspension or in the exchange bed under the stated reaction conditions. Subsequently, the products can be directly used for its ultimate purpose or it can be processed according to known techniques such as filtration, centrifugation and/or decantation in order to be separated from the liquid phase, washed and dried at room temperature or at elevated temperature to 250° C., optionally under vaccum, it may further be optionally tempered at a temperature of 150° to 400°, ground as well as classified, in which certain measures may be omitted or can be carried out in another reaction sequence.

A further method for the preparation of platinum containing compostions according to formula (1) can be carried out by utilizing a polymeric organosiloxane amine compound as shown in DE-OS No. 31 20 214 which consists of entities of the formula:

(3)

wherein $R^1$, $R^2$ and $R^3$ have the same scope of meaning as in formula (1) and these are reacted with stoichiometrically insufficient or excess amounts of $H_2PtCl_6$ or $H_2PtBr_6$, optionally containing water of crystallization, in water or an organic solvent material, in particular, an alcohol having 1 to 5 carbon atoms, in accordance with static or dynamic principles at room temperature or elevated temperature according to a reaction scheme of an acid-base reaction, thereafter the product can be separated from the liquid phase, washed, optionally dried, as well as ground, classified and tempered, optionally in any desired reaction sequence.

The reaction conditions of this method of preparation coincide with those that have already been described above. That applies as well as for the ion exchange as well as also for the subsequently carried out processing steps.

The compounds that are obtained in accordance with the present invention by the above described procedures and having entities of the formula (1) can be modified by after treatment −100° to 350° C. under pressure. Temperatures below normal temperature can be used, such as, by the utilization of low boiling reduction materials such as borane. This can be carried out either directly after the introduction of the complex platinum anion or first after the washing, drying, grinding, classification and tempering of the formed solid material has occurred.

Generally, it is also possible to prepare the platinum and/or palladium containing organosiloxane-ammonium compounds in accordance with the invention through yet another procedure which begins with the monomeric precursors of the as yet metal-free organosiloxane-ammonium compounds. After that, there follows the introduction of the complex platinum or palladium anions; that is to say the ion exchange, while in homogeneous phase through conversion of the monomeric ammonium compounds as is described in the DE-OS No. 31 20 195, with the platinum or palladium containing starting compound and subsequently there is then carried through the polycondensation of the already metal loaded ammonium compound. This procedure has, however, the disadvantage that on the one hand the metal introduction is not so easily carried out because both reaction components are in the liquid phase and on the other hand, after the subsequent polycondensation, the complex metal anion is no longer freely movable and no longer accessible. These disadvantages do not arise with the two previously described procedures.

Considered from the standpoint of their physical properties, the polymeric platinum and/or palladium containing organosiloxane-ammonium compounds of the present invention resemble in some respect special silicas or silica gels and possess, depending on the prior treatment specific surface areas of 0.1 to 2000 m²/g and particle diameter size ranges of about 1 cm to about 1 μm. In air, they are stable up to over 200° C. Under protective gas atmosphere, the thermal stability is noticeably higher, sometimes up to over 400° C.

While the platinum containing organopolysiloxane-ammonium compounds of the invention are valuable catalyst systems for hydrosilylation and hydrogenation reactions, the described palladium containing compounds of the present invention are useful also, particularly as active hydrogenation catalysts. In such applications, they can be used either in unmodified form or after first being subjected to a reduction treatment as described in accordance with the procedures set forth above.

The hydrosilylation of olefinic and acetylenic compounds; that is, the addition of hydrogen silanes onto unsaturated hydrocarbon compounds can be carried out under reaction conditions either above or below room temperature up to a temperature of 300° C. at normal pressure or under superpressure which is the sum of the partial pressures of the individual components of the reaction mixture. In actual use, the catalyst of the present invention can be introduced into a solid bed or into a suspension. Catalysts of the invention exhibit themselves in respect of high activity and selectivity and through a long period of useful life. As a result of their high selectivity, the compounds of the invention may be used under controlled predetermined reaction conditions for hydrosilylation preferably of compounds with active double bonds, as well as compounds with three reactive bonds.

In the hydrogenation aspect, the platinum and/or palladium containing organopolysiloxanes of the invention can, in principle, be introduced where analogous metal compounds particularly metals in homogeneous or heterogeneous phase are also introduced, for example, for the hydrogenation of hydrocarbon polyunsaturated compounds, carbonyls or nitrogen compounds through hydro-halogenation or for hydrogenation of molecular oxygen, whereby depending on the choice of specific reaction conditions, high selectivity can again be obtained.

In general, these hydrogenations can be carried out at room temperature or elevated temperature, using pressure below atmospheric, or atmospheric pressure or superatmospheric pressure. Because of the practical molecular dispersivity, these new hydrogenation catalysts can be developed with a very high activity and at the conclusion of the catalyst process they may be easily separated and recovered from the left over ingredients of the reaction mixture and then newly introduced into the system.

The invention is further explained with reference to the following detailed examples considered from the viewpoint of the primarily important raw materials.

EXAMPLE 1

25 g of a polymeric organosiloxane-ammonium compound consisting of units of the formula:

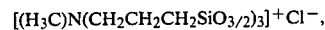

having a particle size of 0.05 to 0.2 mm are suspended in 50 ml of saline water. This suspension in three charges of 200 ml each is reacted with a total of 600 ml of an aqueous solution which contains a total of 16.55 g $K_2PtCl_4$ (39.9 mMol Pt). The solid material was stirred with each charge for 3 hours at 60° C. in a glass beaker with a KPG-stirrer, then filtered off from the liquid phase, washed three times with 300 ml desalted water and was next predried for 5 hours at 90° C. Subsequently, the brown product was dried at 12 hours at 150° C. at 80 mbar to finely divided form.

With the complete loading of the polymeric ammonium compound with $PtCl_4^{2-}$ units, the yield of polymeric product was 34.6 g which approximately consists of units of the formula:

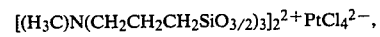

with a Pt content of 20.32 weight percent to be anticipated. There was weighed out 34.0 g with a platinum content of 18.55 weight percent which means that the ion exchanger to the extent of over 91% of the theoretical capacity was saturated with platinum.

EXAMPLE 2

30 g of an organopolysiloxane-ammonium compound formed of units of the formula:

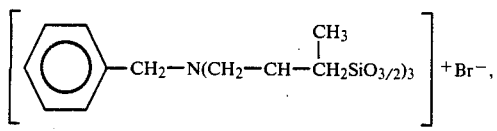

with a particle size of 0.05 to 0.4 mm was treated analogously to Example 1 in two charges with 8.11 g (NH$_4$)$_2$PtBr$_4$, dissolved in 500 ml of desalted water and then converted. After the drying, there was obtained 35.1 g of solid material with a platinum content of 8.10 weight percent. This means an approximately 50% saturation of the ion exchanger with PtBr$_4^{2-}$-entities was obtained.

EXAMPLE 3

30 g of an organopolysiloxane-ammonium compound, containing units of the formula:

having a particle size of 0.05–0.1 mm were converted analogously to Example 1, all at once, with 1.12 g Na$_2$PtCl$_6$, dissolved in 300 ml desalted water. After drying, there was obtained 30.7 g solid material with a Pt-content of 1.52 weight percent. This corresponds to an approximately 10% saturation of the original ion exchanger in the SO$_4^{2-}$ form.

EXAMPLE 4

40 g of an organopolysiloxane-ammonium compound consisting of units of the formula:

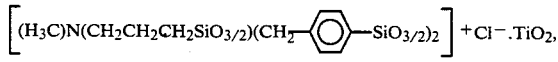

having a particle size of 0.4 to 0.6 mm was dispersed in 200 ml of desalted water and after 1 hour was sent through an ion exchange column with an inner diameter of 23 mm. Subsequently, there is sent through the column at room temperature, five charges having a total of 500 ml of an aqueous solution with a total content of 31.7 g of K$_2$PtCl$_4$ within 3 hours. Then the column contents were washed with a total of 1 liter of desalted water, and then carried over to a vessel and were dried for 24 hours at 120° C. at 80 mbar. There was anticipated to be a platinum content in the obtained solid material of 14.87 weight percent based on a complete conversion of the polymeric entities into units of the formula:

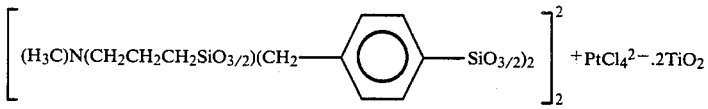

There was actually obtained 50.1 g solid material with a platinum content of 14.7 weight percent.

EXAMPLE 5

25 g of an organopolysiloxane-ammonium compound formed of units of the formula:

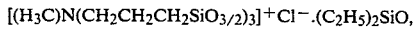

having a particle size of 0.05 to 0.2 mm were treated analogously with regard to Example 1, in two charges, with a total of 4.10 g Na$_2$PdCl$_4$, dissolved in 400 ml desalted water. Subsequently, it was filtered off, washed and dried. There could be obtained 27.3 g of an organopolysiloxane-ammonium compound in that approximately one-half of all chloride ions of the raw material compound can be exchange as against PdCl$_4^{2-}$ ions. The Pd-content; 5.4 weight percent (theoretical: 5.39 weight percent).

EXAMPLE 6

20 g of an organopolysiloxane-ammonium compound containing units of the formula:

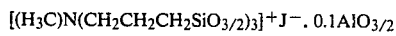

with a particle size of 0.05–0.1 mm were treated in accordance with Example 1, in three charges, with a total of 13.4 g K$_2$PdCl$_6$, dissolved in 400 ml of desalted water. Subsequently, this was filtered, washed and dried. There was obtained 21.4 g of an organopolysiloxane-ammonium compound, the anticipated amount of the Pd-content was 10.85 weight percent with an approximately complete saturation with PdCl$_6^{2-}$ ions. (Theoretical Pd-content with complete saturation 11.17 weight percent.)

EXAMPLE 7

30 g of an organopolysiloxane-ammonium compound containing units of the formula:

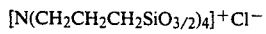

with a particle size of 0.05–0.1 mm was treated in accordance to Example 1 in two charges with a total of 2.92 g K$_2$PtCl$_4$ dissolved in a 100 ml of desalted water. Subsequently, this was filtered off, washed and dried. There was obtained 31.7 g of organopolysiloxane-ammonium compound in which approximately a fifth of all chloride ions of the starting material were exchanged against PtCl$_4^{2-}$ ions. The platinum content was 4.25 weight percent (theoretical 4.31 weight percent).

EXAMPLE 8

30 g of an organopolysiloxane-amine compound containing units of the formula:

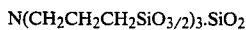

with a particle size of 0.05–0.1 mm were treated analogously to Example 1 in three charges with a total of 7.55 g H$_2$PtCl$_6$ dissolved in 300 ml ethanol, treated at reflux temperature, then filtered and subsequently washed with 500 ml ethanol and then dried for 15 hours at 80° C./80 mbar. There was obtained 37.3 g of an organopolysiloxane compound in which approximately one-half of all of the amine units of the starting raw material were now present as units of the formula:

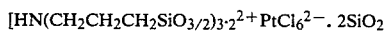

Platinum content 9.30 weight percent (theoretical 9.57 weight percent).

EXAMPLE 9

25 g of an organpolysiloxane-ammonium compound containing units of the formula:

[(H$_3$C)N(CH$_2$CH$_2$CH$_2$SiO$_{3/2}$)$_3$]$^+$OH$^-$, having a particle size 0.4–0.6 mm were treated analogously to Example 4 in 200 ml isopropanol and are conveyed over into an ion exchange column. Subsequently, the column was charged in five charges with a total of 18.7 g H$_2$PtCl$_6$, dissolved in 500 ml isopropanol, within 3 hours. Then the product was washed with 500 ml isopropanol and dried for 24 hours at 120° C./80 mbar. There was obtained 38.3 g of organopolysiloxane-ammonium compound in which approximately all OH$^-$ ions were exchanged for PtCl$_6^{2-}$. Pt-content 18.0 weight percent (theoretical 18.9 weight percent).

EXAMPLE 10

30 g of an organopolysiloxane-ammonium compound, containing units of the formula:

[(H$_3$C)N(CH$_2$CH$_2$CH$_2$SiO$_{3/2}$)$_3$]$^+$Cl$^-$, with a particle size of 0.05–0.1 mm, were treated analogously to Example 1 in three charges with a total of 4.49 g K$_2$PtCl$_4$ and 3.18 g Na$_2$PdCl$_4$ dissolved together in 300 ml desalted water. Subsequently, this was filtered off, washed and dried. There was obtained 34.5 g (theoretical 34.79 g) of an organopolysiloxane-ammonium compound in which approximately half of all chloride ions of the starting raw material were exchanged against PtCl$_4^{2-}$ and PdCl$_4^{2-}$. Pt-content 5.82 weight percent (theoretical 6.06 weight percent). Pd-content 3.17 weight percent (theoretical 3.31 weight percent).

EXAMPLE 11

6.0 g of the platinum containing organopolysiloxane-ammonium compound prepared in accordance with Example 1 and containing essentially units of the formula:

[(H$_3$C)N(CH$_2$CH$_2$CH$_2$SiO$_{3/2}$)$_3$]$_2^{2+}$PtCl$_4^{2-}$, with a Pt-content of 18.55 weight percent and a particle size of 0.05–0.2 mm were suspended in 100 ml ethanol. The brown/black suspension was heated up to reflux temperature and then was converted under vigorous stirring of 1 hour with a solution of 1.0 g NaBH$_4$ in 100 ml ethanol. The suspension was agitated under reflux for an additional 2 hours. Subsequently, the solid material was filtered off and conveyed over to an extraction column. After 5 hours of extraction with an ethanol/water mixture of 1:1, the gray/black product was conveyed to a flask. It was then dried for 15 hours at 120° C./80 mbar and then stored under nitrogen and preserved. The weighed product was 5.8 g, Pt-content 18.8 weight percent.

EXAMPLE 12

10 g of a palladium containing organopolysiloxane-ammonium compound prepared in accordance with a procedure analogous to Example 5 and containing units of the formula:

[(H$_3$C)N(CH$_2$CH$_2$CH$_2$SiO$_{3/2}$)$_3$]$_2^{2+}$PdCl$_4^{2-}$. 2SiO$_2$, and having a Pd-content of 10.7 weight percent was treated analogously to Example 11 with 10 ml 37% formaldehyde solution. After a 15 hour drying at 120° C. at 80 mbar, there was obtained 9.3 g of product with a Pd-content of 11.2 weight percent.

EXAMPLE 13

10 g of a platinum and palladium containing organopolysiloxane-ammonium compound obtained in accordance with Example 10 were suspended in 100 ml of methanol. The suspension was conveyed over to a 500 ml hub autoclave and there treated for 2 hours with a hydrogen pressure of 50 bar and a temperature of 120° C. Subsequently, the autoclave was opened and the product was washed with a total of 100 ml methanol, dried for 8 hours at 100° C./80 mbar and then preserved under nitrogen. The weighed product was 9.5 g with a Pt-content of 5.6 weight percent, a Pd-content of 3.02 weight percent.

EXAMPLE 14

30 ml toluol, 22.35 g (300 mMol) proparglychloride and 42.7 g (315 mMol) trichlorsilane and 0.59 g of the platinum containing organopolysiloxane-ammonium compound obtained according to Example 1 was introduced into a 100 ml three neck flask which is stirred with a magnetic stirring rod. The mixture was heated up to reflux temperature was approximately 50° C. The reflux temperature within about 6 hours rose from 50° C. to 118° C. It was cooled off and the solution was inspected using NMR-spectroscopy and gas chromatography. It was determined that the starting compounds had completely disappeared and that the product was the compound SiCl$_3$—CH$_3$=CH—CH$_2$Cl, with over 95% selectivity as established through gas chromatography and NMR-comparative inspection.

Under the chosen reaction conditions, the high selectivity of the utilized catalysts resulted in almost exclusive triple bond hydrosilylation because the formed double bond could not be attacked. With the corresponding comparative experiments with a conventional Pt/C hydrosilylation catalyst and with H$_2$PtCl$_6$ there was no comparable result obtained, indeed, in that case, hydrosilylation of the trifunctional as well as the double bond was obtained.

EXAMPLE 15

4.36 ml acrylic acid ethylester, 20 ml toluol and 40 mg of the catalyst prepared in accordance with Example 13 were introduced into a 50 ml flask. This flask was connected to a hydrogenation apparatus. Under magnetic agitation at a temperature of 80° C. and with an absolute hydrogen pressure of approximately 1 bar, the acrylic acid ethylester was completely converted within 50 minutes after a takeup of 970 ml hydrogen to propionic acid ethylester without the hydrogenation of the toluol or reduction of the ester group.

EXAMPLE 16

4.36 ml acrylic acid ethylester, 3 ml hexene-1, 20 ml toluol and 40 mg of the Pt containing catalyst obtained in accordance with Example 1 was converted with hydrogen analogously to Example 15. Within 90 minutes, the acrylic acid ethylester was converted to propionic acid ethylester without the utilized hexene-1 being in any determinable degree hydrogenated to hexane.

In this case, the utilized catalyst exhibited a restricted activity relative to that in Example 15, and as a result there was observable a higher selectivity for activated double bonds.

EXAMPLE 17

A hydrogenation analogous to Example 16 was carried out with an equivalent amount of the palladium catalyst obtained in accordance with Example 5 which eventually gave a complete hydrogenation of the acrylic acid ethylester to propionic acid ethylester wherein at the same time, the hexene-1 was not hydrogenated over 90%.

Further modifications and variations of the foregoing invention will be apparent to those skilled in the art from a study of the foregoing detailed description and which are intended to be encompassed by the claims appended hereto.

The entire disclosure of the German application P No. 34 04 702.6-44 is relied on and incorporated herein by reference.

We claim:

1. A platinum and/or palladium containing organopolysiloxane-ammonium compounds comprising at least one unit and is represented by the structural formula:

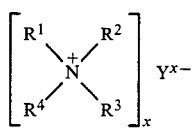 (1)

wherein $R^1$, $R^2$ and $R^3$ are the same or different and represent the structural formula:

$$R^5-SiO_{3/2} \quad (2)$$

wherein $R^5$ is a linear or branched chain alkylene containing from 1 to 12 carbon atoms, cycloalkylene with 5, 7, or 8 carbon atoms or a member represented by the structural formula:

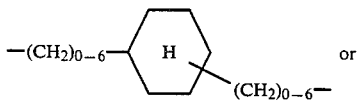 or

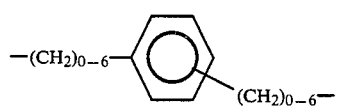

and the free valences of the oxygen atom are saturated either by silicon atoms or additional groups of the formula (2) and/or crosslinking bridging agents having the formula:

$SiO_{4/2}$, $SiR'O_{3/2}$, $SiR_2'O_{2/2}$,
$TiO_{4/2}$, $TiR'O_{3/2}$, $TiR_2'O_{2/2}$,
$AlO_{3/2}$, $AlR'O_{2/2}$ wherein
R' is methyl or ethyl and the relationship between silicon in formula (2) to the bridging atoms silicon, titanium and aluminum ranges from 1:0 to 1:10,
$R^4$ has the same meaning as $R^1$, $R^2$ and $R^3$ and can also be hydrogen, linear or branched alkyl chain of 1 to 10 carbon atoms, cycloalkyl of 5 to 8 carbon atoms or benzyl, $Y^{x-}$ represents at least one Pt or Pd containing member from the group consisting of:
$PtCl_4^{2-}$, $PtCl_6^{2-}$,
$PtBr_4^{2-}$, $PtBr_6^{2-}$,
$PdCl_4^{2-}$, $PdCl_6^{2-}$,
$PdBr_4^{2-}$, $PdBr_6^{2-}$ the corresponding salt thereof with an inorganic or organic, 1 to 3 valent anion of an inorganic or organic protonic acid which is capable of reacting with an amine to form a stable salt, and the corresponding hydroxy group terminated member
and
x is a number from 1 to 3.

2. The polymeric organosiloxane-ammonium compound according to claim 1 further comprising that a plurality of complex anions of platinum and/or palladium are contained in the polymeric system.

3. The polymeric organosiloxane-ammonium compound according to claim 1 wherein the molar ratio between platinum and/or palladium containing anions to the rest of the inorganic or organic 1 to 3 valent anions ranges from 1:0 to 1:100.

4. The polymeric organosiloxane-ammonium compound according to claim 1 further comprising that $R^1$, $R^2$ and $R^3$ are each identical and that $R^4$ is methyl.

5. The polymeric organosiloxane-ammonium compound according to claim 1 wherein the compound comprising polymer units of the formula:

$$[(H_3C)N(CH_2CH_2CH_2SiO_{3/2})_3]_x{}^+Y^{x-}.$$

6. A platinum and/or palladium containing polymeric organosiloxane-ammonium compound which is produced by treating an organopolysiloxane-ammonium compound with a reducing agent at total pressures ranging from of 1 to 300 bar and at a temperature of from $-100°$ to $350°$ C., wherein said organopolysiloxane-ammonium compound is represented by formula (I) herein.

7. A method for the preparation of platinum and/or palladium containing polymeric organosiloxane-ammonium compounds comprising reacting an organopolysiloxane-ammonium compound according to formula (I):

 (1)

wherein $R^1$, $R^2$ and $R^3$ are the same or different and represent the structural formula:

$$R^5-SiO_{3/2} \quad (2)$$

wherein $R^5$ is a linear or branched chain alkylene containing from 1 to 12 carbon atoms, cycloalkylene with 5, 7 or 8 carbon atoms or a member represented by the structural formula:

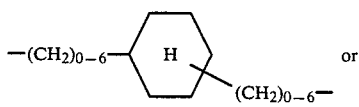

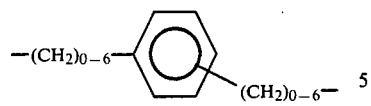

and the free valences of the oxygen atom are saturated either by silicon atoms or additional groups of the formula (2) and/or crosslinking bridging agents having the formula:

SiO$_{4/2}$, SiR'O$_{3/2}$, SiR$_2$'O$_{2/2}$,
TiO$_{4/2}$, TiR'O$_{3/2}$, TiR$_2$'O$_{2/2}$,
AlO$_{3/2}$, AlR'O$_{2/2}$ wherein
R' is methyl or ethyl and the relationship between silicon in formula (2) to the bridging atoms silicon, titanium and aluminum ranges from 1:0 to 1:10,
R$^4$ has the same meaning as R$^1$, R$^2$ and R$^3$ and can also be hydrogen, linear or branched chain alkyl of 1 to 10 carbon atoms, cycloalkyl of 5 to 8 carbon atoms or benzyl, wherein Y$^{x-}$ represents a 1 to 3 functional anion of an inorganic or organic protonic acid,
wherein Y$^{x-}$ represents a 1 to 3 valent anion of an inorganic or organic protonic acid which is capable of reacting with an amine to form a stable salt,
with a stoichiometric excess or insufficiency of a compound represented by the formula:
M$_2$PtCl$_4$, M$_2$PtCl$_6$,
M$_2$PtBr$_4$, M$_2$PtBr$_6$,
M$_2$PdCl$_4$, M$_2$PdCl$_6$,
M$_2$PdBr$_4$, M$_2$PdBr$_6$,
or the corresponding water of crystallization containing compound wherein M represents lithium, sodium, potassium, ammonium or hydrogen,
in water or a polar organic solvent
wherein the platinum or palladium compound is at least partially soluble
for the mutual partial or complete exchange of the anions according to the static or dynamic principle,
and washing the metal containing solid material.

8. The method according to claim 7 further comprising separating the solid material from the liquid phase and thereafter drying the material.

9. The method according to claim 7 further comprising grinding, classifying and tempering for a time period of 1 hour to 4 days at a temperature of 150° to 400° C.

10. The method according to claim 9 further comprising tempering under vacuum.

11. The method according to claim 7 wherein the product is dried and ground, classified and tempered at a temperature of 150° to 400° C.

12. The method according to claim 8 wherein the material is tempered in a time period extending from about 1 hour to about 4 days.

13. The method according to claim 12 wherein the tempering is carried out under vacuum.

14. The method according to claim 7 further comprising simultaneously or sequentially carrying out the reaction with a plurality of at least partially dissolved starting compounds of platinum and/or palladium and wherein the metal containing solid material formed as a result of said reaction is subsequently removed from the liquid phase, washed and dried.

15. The method according to claim 14 wherein the solid material is tempered.

16. The method for the preparation of a platinum containing polymeric organosiloxane-ammonium compound comprising reacting a polymeric organosiloxane-ammonium compound represented by the recurring units of having the formula:

wherein R$^1$, R$^2$ and R$^3$ represent a group having a structural formula:

$$R^5\text{—SiO}_{3/2} \qquad (2)$$

in which R$^5$ is linear or branched chain alkyl containing from 1 to 12 carbon atoms, cycloalkyl having 5, 7 or 8 carbon atoms or a member represented by the formula:

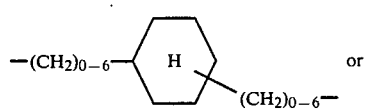 or

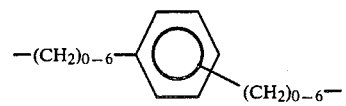

wherein R$^1$, R$^2$ and R$^3$ can be the same or different and the free valences of the oxygen are satisfied either by silicon atoms or additional groups of formula (2) or are satisfied by crosslinking bridging agents having the formulae:

SiO$_{4/2}$, SiR'O$_{3/2}$, SiR$_2$'O$_{2/2}$,
TiO$_{4/2}$, TiR'O$_{3/2}$, TiR$_2$'O$_{2/2}$,
AlO$_{3/2}$, AlR'O$_{2/2}$ wherein R' represents methyl or ethyl and the ratio between the silicon atom in formula (2) to the bridging atoms silicon, titanium and aluminum ranges from 1:0 to 1:10,
with a stoichiometrically insufficient or excess amount of H$_2$PtCl$_6$ or H$_2$PtBr$_6$
or the corresponding water of crystallization containing materials
in water or in a lower alcohol having 1 to 5 carbon atoms
according to static or dynamic principles at room temperature or at elevated temperature until a conversion is achieved and the desired product is obtained.

17. The method according to claim 16 wherein the solid metal containing material is removed from the liquid phase and is dried and recovered.

18. The method according to claim 16 wherein the solid is ground, classified and tempered.

19. The method according to claim 18 wherein the tempering is carried out at a temperature of 150° to 400° C.

20. The method according to claim 18 wherein the tempering is carried out from 1 hour to 4 days.

21. The method according to claim 18 wherein the tempering is carried out under vacuum.

22. The method according to claim 16 wherein the recovered solid material is subsequently treated at a pressure of 1 to 300 bar and a temperature of −100° to 300° C. in the presence of a reduction agent.

23. A catalyst for hydrosilylation or hydrogenation reactions comprising a platinum and/or palladium containing polymeric organosiloxane-ammonium compound according to claim 1.

* * * * *